United States Patent
Pribanic

(10) Patent No.: US 8,550,988 B2
(45) Date of Patent: Oct. 8, 2013

(54) ENDOSCOPIC CLEANER

(75) Inventor: Justin R. Pribanic, Broad Brook, CT (US)

(73) Assignee: Covidien LP, Mansfield, MA (US)

(*) Notice: Subject to any disclaimer, the term of this patent is extended or adjusted under 35 U.S.C. 154(b) by 798 days.

(21) Appl. No.: 12/401,036

(22) Filed: Mar. 10, 2009

(65) Prior Publication Data

US 2009/0264703 A1 Oct. 22, 2009

Related U.S. Application Data

(60) Provisional application No. 61/046,554, filed on Apr. 21, 2008.

(51) Int. Cl.
*A61B 1/04* (2006.01)
*B08B 1/00* (2006.01)

(52) U.S. Cl.
USPC ........ 600/121; 600/124; 600/125; 15/104.03; 15/104.04

(58) Field of Classification Search
USPC .......... 600/121, 124, 125, 142, 193; 604/267; 15/104.03, 104.04, 104.05
See application file for complete search history.

(56) References Cited

U.S. PATENT DOCUMENTS

| | | | | |
|---|---|---|---|---|
| 946,370 A | * | 1/1910 | Kelmel | 15/160 |
| 2,850,754 A | * | 9/1958 | Davis | 15/220.4 |
| 3,308,825 A | * | 3/1967 | Cruse | 604/267 |
| 4,281,646 A | | 8/1981 | Kinoshita | |
| 4,543,683 A | * | 10/1985 | Goldman | 15/256.6 |
| 4,643,726 A | * | 2/1987 | Gegelys | 604/368 |
| 4,941,872 A | | 7/1990 | Felix et al. | |
| 5,077,861 A | * | 1/1992 | Bokat | 15/256.5 |
| 5,313,934 A | | 5/1994 | Wiita et al. | |
| 5,337,730 A | | 8/1994 | Maguire | |
| 5,382,297 A | * | 1/1995 | Valentine et al. | 134/15 |
| 5,392,766 A | * | 2/1995 | Masterson et al. | 600/157 |
| 5,735,792 A | | 4/1998 | Vanden Hoek et al. | |
| 5,931,833 A | | 8/1999 | Silverstein | |
| 6,293,907 B1 | * | 9/2001 | Axon et al. | 600/114 |
| 6,354,992 B1 | | 3/2002 | Kato | |

(Continued)

FOREIGN PATENT DOCUMENTS

EP 1210904 6/2002
WO WO 98/24359 6/1998

OTHER PUBLICATIONS

European Search Report for corresponding EP 09251140 date of mailing is Dec. 12, 2009 (3 pages).

*Primary Examiner* — Philip R Smith
*Assistant Examiner* — Rynae Boler

(57) ABSTRACT

A cleaning device for use with a percutaneous visualization device includes a cannula and a cleaning swab. The cannula has a first section pivotably connected to a second section. The cleaning swab is positioned at a distal end of the cannula and is configured to pivot into a position to clean at least a portion of a percutaneous visualization device upon insertion into the cannula. In an alternative embodiment, the cleaning device includes a cannula and a seal. The seal is disposed within the cannula and configured to clean at least a portion of a percutaneous visualization device upon insertion and retraction in the cannula. Further, the cannula has a cleaning surface on at least a portion of an inner surface thereof. The cleaning surface is also configured to clean at least a portion of said percutaneous visualization device upon insertion and retraction in the cannula.

8 Claims, 5 Drawing Sheets

(56) References Cited

U.S. PATENT DOCUMENTS

| | | | |
|---|---|---|---|
| 6,447,444 B1* | 9/2002 | Avni et al. | 600/121 |
| 7,097,629 B2* | 8/2006 | Blair | 604/1 |
| 7,300,445 B2 | 11/2007 | Adams | |
| 7,316,683 B2 | 1/2008 | Kasahara et al. | |
| 7,339,341 B2 | 3/2008 | Oleynikov et al. | |
| 7,361,166 B2* | 4/2008 | Bosse et al. | 604/263 |
| 7,530,984 B2 | 5/2009 | Sonnenschein et al. | |
| 7,762,959 B2* | 7/2010 | Bilsbury | 600/564 |
| 2002/0022762 A1* | 2/2002 | Beane et al. | 600/101 |
| 2002/0065450 A1* | 5/2002 | Ogawa | 600/157 |
| 2003/0073955 A1 | 4/2003 | Otawara | |
| 2003/0199768 A1* | 10/2003 | Cespedes et al. | 600/473 |
| 2004/0031119 A1* | 2/2004 | McKay | 15/227 |
| 2005/0049460 A1* | 3/2005 | Mikkaichi et al. | 600/121 |
| 2005/0197595 A1* | 9/2005 | Huang et al. | 600/567 |
| 2005/0256373 A1* | 11/2005 | Bar-Or et al. | 600/114 |
| 2006/0036277 A1* | 2/2006 | Kieturakis et al. | 606/192 |
| 2006/0199998 A1 | 9/2006 | Akui et al. | |
| 2006/0258909 A1* | 11/2006 | Saadat et al. | 600/121 |
| 2007/0032831 A1* | 2/2007 | Eigler et al. | 607/6 |
| 2007/0208220 A1 | 9/2007 | Carter | |
| 2007/0208221 A1 | 9/2007 | Kennedy, II et al. | |
| 2007/0213667 A1 | 9/2007 | Prusmack | |
| 2007/0282253 A1 | 12/2007 | Sasaki | |
| 2007/0282356 A1 | 12/2007 | Sonnenschein et al. | |
| 2008/0015618 A1 | 1/2008 | Sonnenschein et al. | |
| 2008/0319266 A1 | 12/2008 | Poll et al. | |
| 2009/0112065 A1 | 4/2009 | Harrel | |
| 2010/0030031 A1 | 2/2010 | Goldfarb et al. | |

* cited by examiner

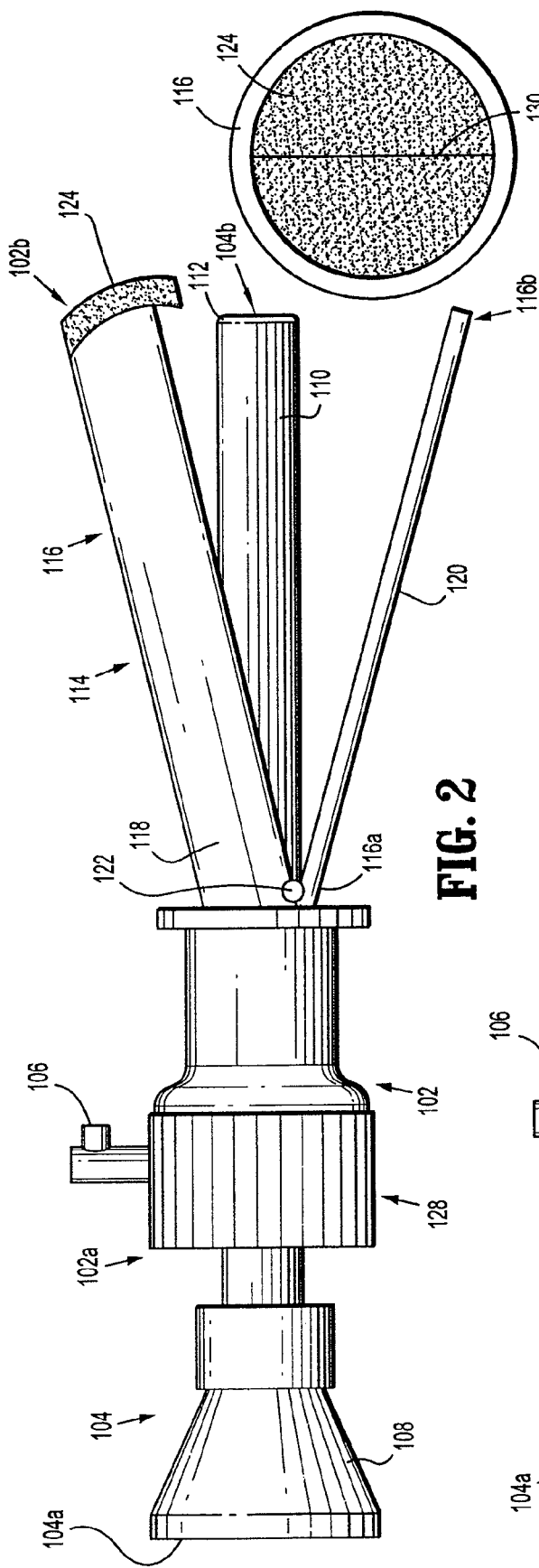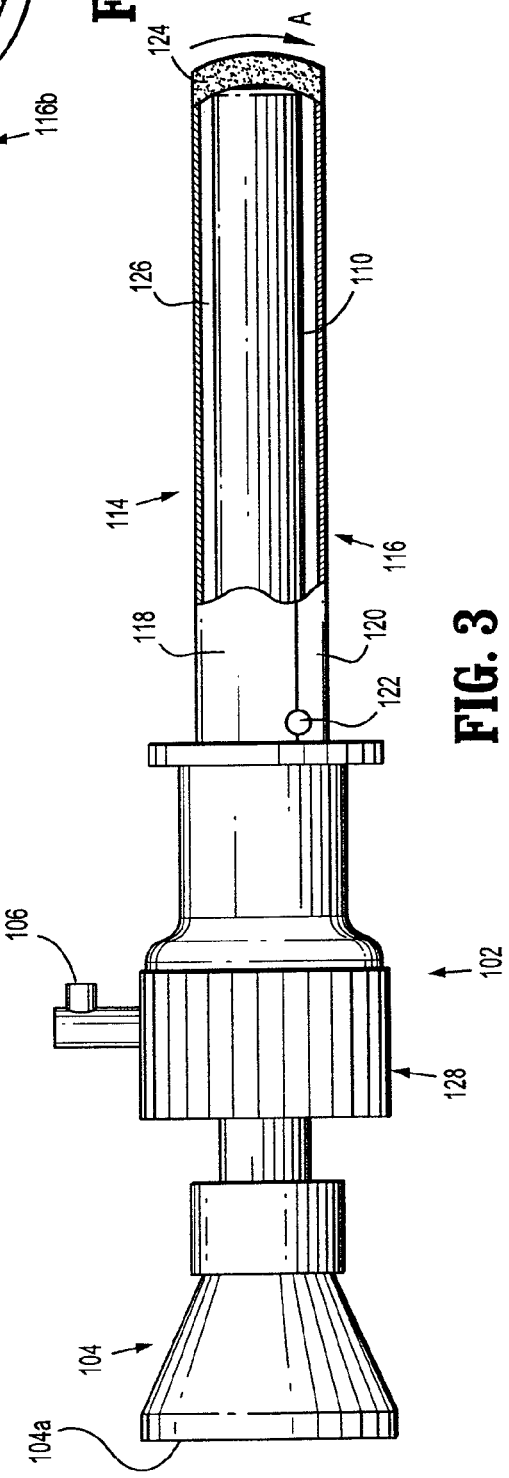

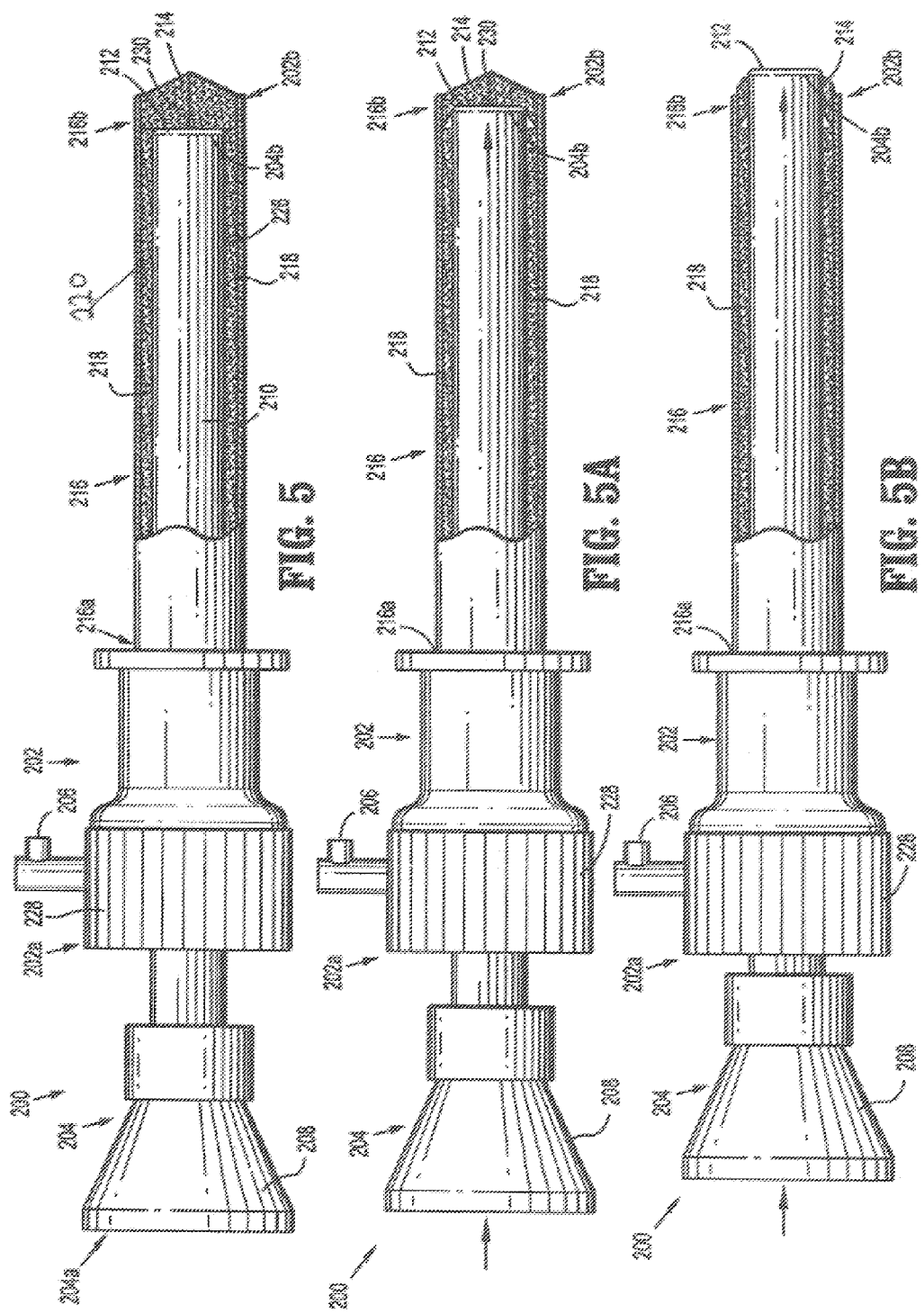

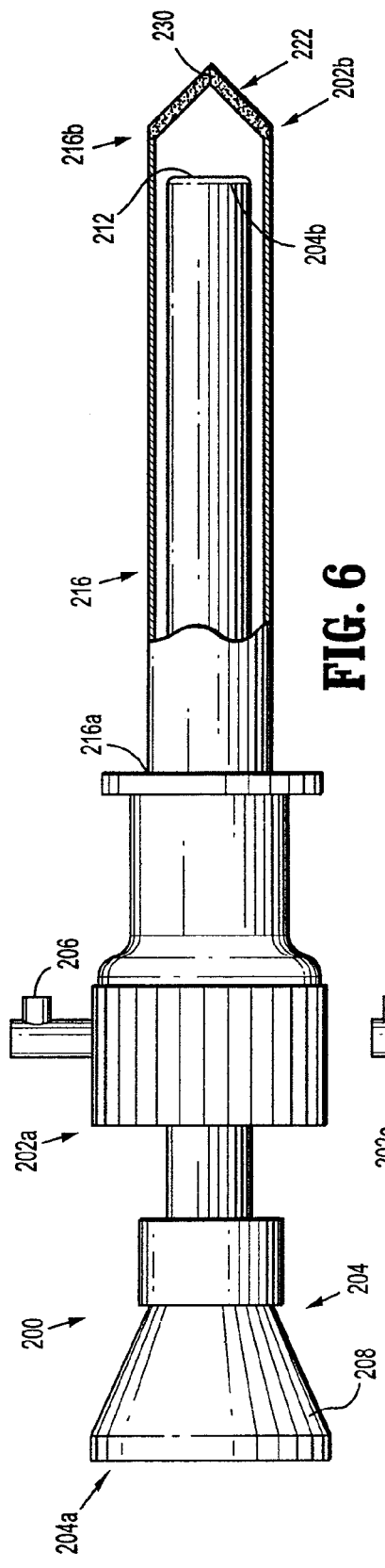
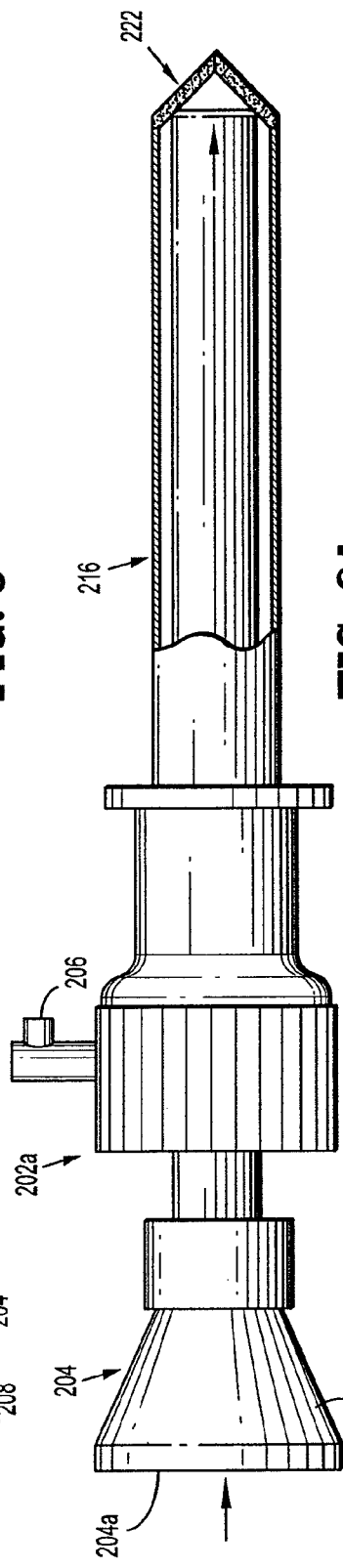
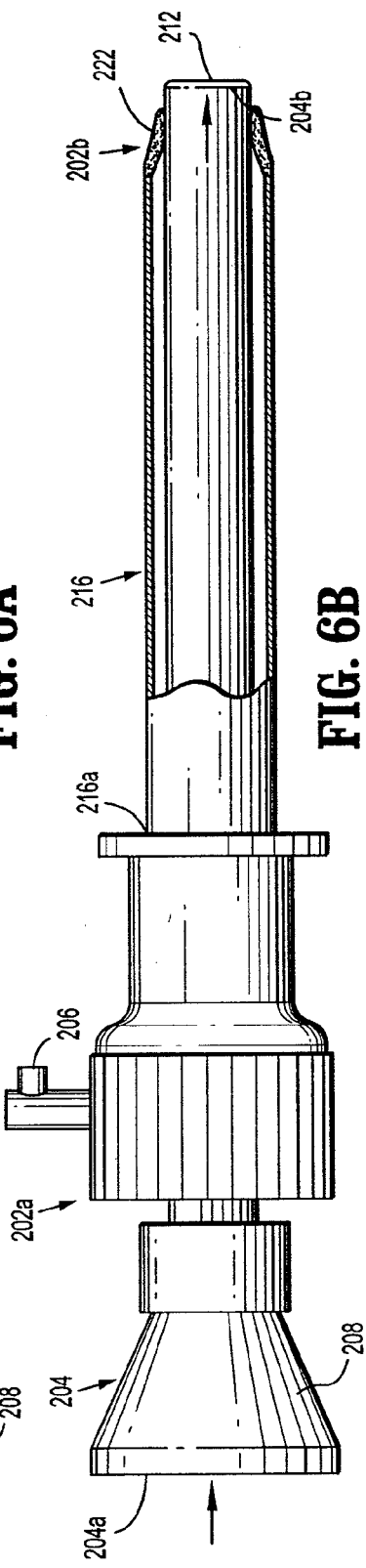

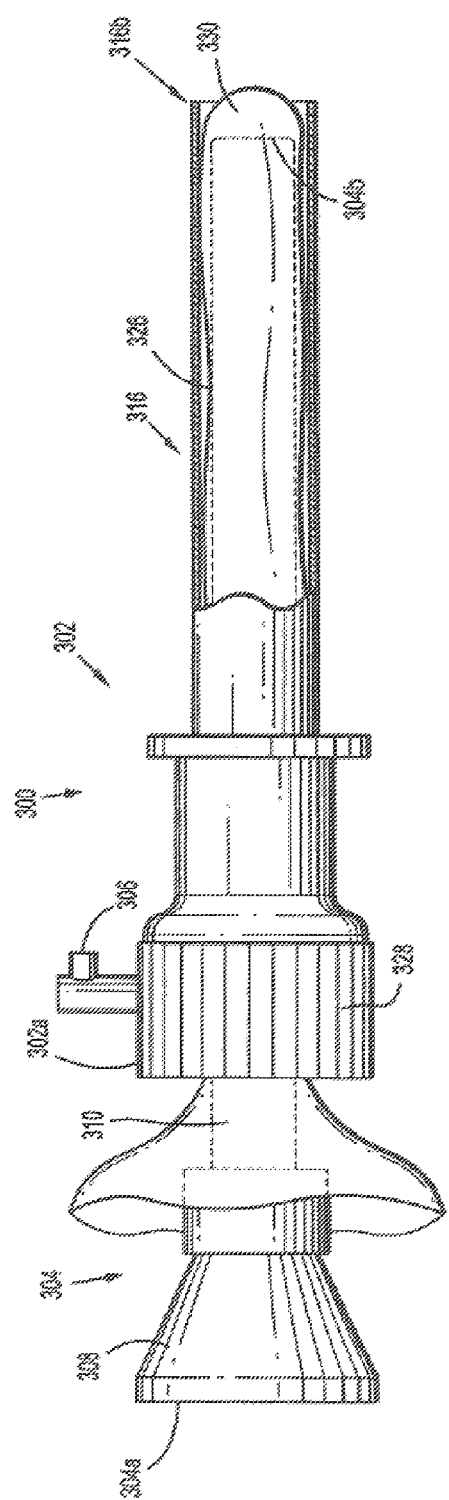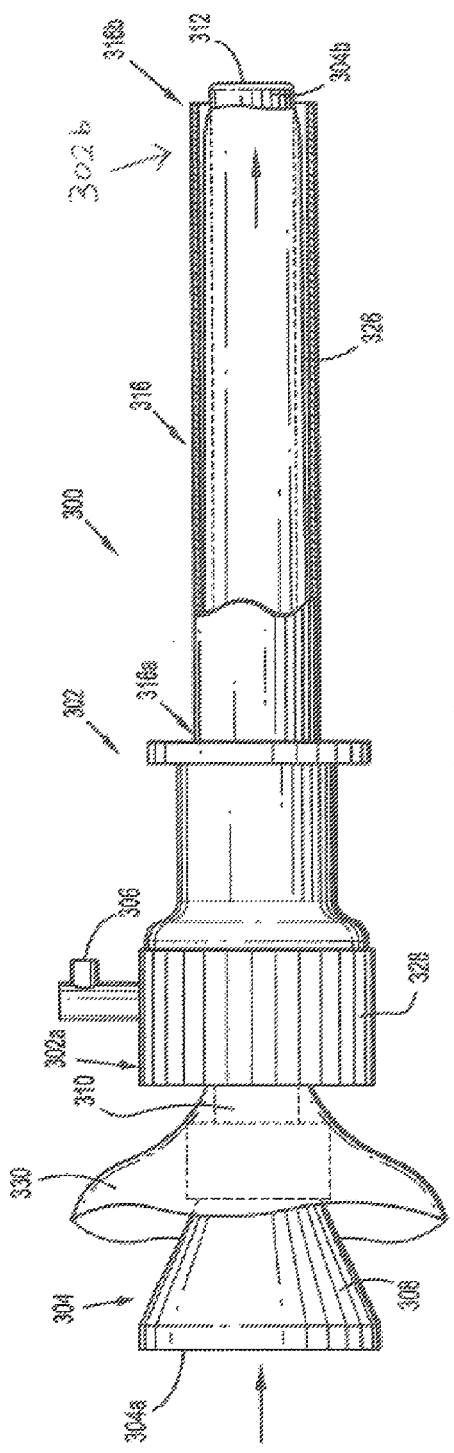

ENDOSCOPIC CLEANER

CROSS REFERENCE TO RELATED APPLICATION

The present application claims the benefit of and priority to U.S. Provisional Application Ser. No. 61/046,554, filed on Apr. 21, 2008, the entire contents of which are incorporated herein by reference.

BACKGROUND

1. Technical Field

The present disclosure relates generally to surgical instruments. More particularly, the present disclosure relates to cleaning devices for use with percutaneous visualization devices.

2. Background of Related Art

Some surgical procedures, namely laparoscopy, hysteroscopy, and endoscopy, require the insertion of a visualization device into a body cavity. During such procedures, surgeons use visualization devices, such as laparoscopes, arthroscopes and endoscopes, to observe features and structures within a body cavity. The view provided by these devices facilitates detection of physiological anomalies within the human body.

Visualization devices typically include a rigid or flexible rod. These rods generally contain light-transmitting fibers and lenses. An external light source usually provides illumination and is ordinarily connected to a proximal end of the rod. The fibers transmit light to the distal end of the visualization device through the rod. After providing adequate illumination, surgeons can inspect the internal structure of a body cavity by observing through an eyepiece, which is ordinarily located at the proximal end of the rod. Alternatively, visualization devices include cameras disposed at their distal end. These cameras transmit video signals to a monitor electrically linked to the rod of the visualization device. Visualization devices with cameras allow doctors to perform surgical procedures while watching a monitor. Doctors, however, must follow certain steps before they can properly use a visualization device.

Before introducing a visualization device into a body cavity, doctors usually insufflate a body cavity with gas or liquid. Thereafter, a sleeve or sheath, often referred to as a trocar, is inserted through the wall of the cavity. These trocars ordinarily include a seal that prevents leakage of gas or liquid from within the body cavity. After the body cavity is properly insufflated, the visualization device is inserted through the trocar. Doctors can then view the inner features of the body cavity through the visualization device disposed within the trocar.

Trocars are not necessarily operatively coupled to a specific visualization device. One trocar is often used with multiple visualization devices. To use a different visualization device, a surgeon can simply retract a visualization device positioned within the trocar and insert another visualization device through the same trocar. Alternatively, the trocar may have multiple ports.

While extracting and inserting a visualization device, bodily fluids and debris can enter the inner portions of the trocar. These fluids and debris may stick to the surfaces of the newly inserted visualization device and soil the lens thus reducing visibility through the lens.

The most common approach to dealing with obscured lenses has been to remove the visualization device and to manually clean it. While effective, the need to withdraw the visualization device from the trocar, clean it, reinsert it, and relocate the target, is highly inefficient and has the potential to increase the risk of infection. Others have proposed to incorporate a spray wash nozzle on the visualization device itself to permit cleaning of the lens without removing the visualization from the patient. The proposed visualization devices, however, may be relatively expensive and require the provision of irrigation passages and cleaning fluids.

For the foregoing reasons, it would be desirable to provide inexpensive devices and methods for cleaning visualization devices without removing the visualization device from the trocar.

SUMMARY

The present disclosure relates to cleaning devices for use with a percutaneous visualization device. An embodiment of the presently disclosed cleaning device includes a cannula and a cleaning swab. The cannula has a proximal end, a distal end, a first section and a second section. The first section of the cannula is pivotably connected to the second section. The cleaning swab is positioned at the distal end of the cannula and is configured to pivot into a position to clean at least a portion of a percutaneous visualization device upon insertion in the cannula.

Another embodiment of the cleaning device includes a cannula and a seal. The cannula has a proximal end and a distal end. The seal is disposed within the cannula and is configured to clean at least a portion of a percutaneous visualization device upon insertion and retraction in the cannula. The cannula further includes a cleaning surface on at least a portion of an inner surface thereof. The cleaning surface is also configured to clean at least a portion of the percutaneous visualization device upon insertion and retraction in the cannula.

Still another embodiment of the cleaning device includes a cannula and at least one cleaning surface. The cannula has a proximal end and a distal end. The cleaning surface is disposed at a distal portion of the cannula and is configured to clean at least a portion of a percutaneous visualization device upon insertion and retraction in the cannula.

In an alternative embodiment, the cleaning device includes a cannula having a proximal and a distal end. This embodiment also includes a sleeve adapted to surround at least a portion of a percutaneous visualization device. The sleeve is configured to be insertable into the cannula and then removed from the visualization device through the cannula.

BRIEF DESCRIPTION OF THE DRAWINGS

Various embodiments of the presently disclosed surgical instruments and cleaning devices are described herein with reference to the drawings, wherein:

FIG. 2 is a side elevational view of the surgical instrument of FIG. 1 in the open position;

FIG. 3 is a side elevational view of the surgical instrument of FIG. 1 in the closed positioned;

FIG. 4 is a front elevational view of the surgical instrument of FIG. 1;

FIG. 5 is a side elevational view of a surgical instrument according to an embodiment of the present disclosure;

FIG. 5A is a side elevational view of the surgical instrument of FIG. 5 with an endoscope abutting a cleaning seal;

FIG. 5B is a side elevational view of the surgical instrument of FIG. 5 with the endoscope passing through the cleaning seal;

FIG. 6 is a side elevational view of a surgical instrument according to an embodiment of the present disclosure;

FIG. 6A is a side elevational view of the surgical instrument of FIG. 6 with an endoscope abutting seal wipes;

FIG. 6B is a side elevational view of the surgical instrument of FIG. 6 with an endoscope passing through the seal wipes;

FIG. 7 is a side elevational view of a surgical instrument according to an embodiment of the present disclosure; and FIG. 8 is a side elevational view of the surgical instrument of FIG. 7.

DETAILED DESCRIPTION OF THE DRAWINGS

Figure 1:
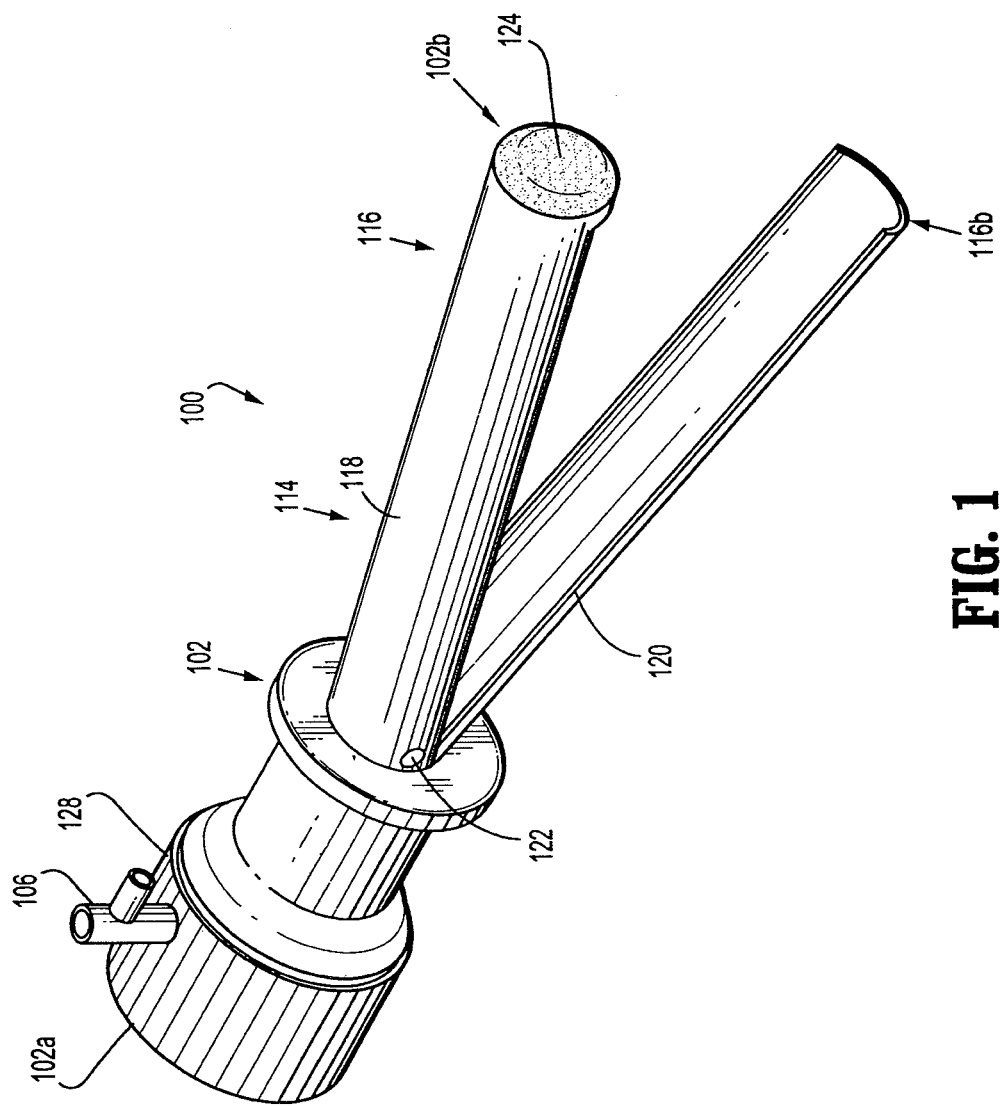
FIG. 1 is a perspective view of a surgical instrument and a cleaning device according to an embodiment of the present disclosure.

Embodiments of the presently disclosed surgical instruments and cleaning devices are described in detail with reference to the drawings, in which like reference numerals designate identical or corresponding elements in each of the several views. In the drawings and in the description that follows, the term "proximal," as is traditional, will refer to the end of the cleaning device, or portion thereof, that is closest to the operator while the term "distal" will refer to the end of the cleaning device that is farthest from the operator. Also, as used herein, all singular forms, such as "a," "an," and "the" are intended to include the plural forms as well, unless expressly stated otherwise. Likewise, all plural references include the singular forms.

Referring initially to FIGS. 1-3, a surgical instrument is generally designated as reference numeral 100. Surgical instrument 100 includes a percutaneous visualization device 104. Percutaneous visualization device 104 can be an endoscope, a laparoscope or any suitable device designed for visual inspection of a body's internal structure. In general, percutaneous visualization device 104 includes a handle 108, a tubular member 110, and a viewing lens 112. Handle 108 is located at a proximal end 104a of percutaneous visualization device 104. Lens 112, in turn, is disposed at a distal end 104b of percutaneous visualization device 104. Tubular member 110, which interconnects handle 108 and lens 112, is adapted to transmit light therethrough. In one embodiment, percutaneous visualization device 104 includes a camera configured to transmit video signals to an external monitor. It is envisioned that the specific structural features of percutaneous visualization device 104 are immaterial insofar as the device facilitates visual inspection of the inner structures of a human body.

Surgical instrument 100 also includes a trocar 102 having a proximal end 102a and a distal end 102b. The present disclosure contemplates that trocar 102 can be substituted for a sleeve, sheath or any other suitable apparatus capable of providing percutaneous access into a body. Nevertheless, trocar 102 particularly includes an insufflation valve 106 located at proximal end 102a of trocar 102. Although the drawings illustrate an insufflation valve 106, those skilled in the art will recognize that other suitable apparatuses can be used for providing fluid access to trocar 102. Trocar 102 additionally includes a handle 128 disposed at proximal end 102a. In operation, users may grab handle 128 to guide the movement of trocar 102.

In addition to handle 128, trocar 102 includes a cleaning device 114 adapted to clean at least a portion of the percutaneous visualization device 104. Cleaning device 114 has a cannula 116 including a proximal end 116a, a distal end 116b, a first section 118, a second section 120, and a bore 126 disposed therethrough. Bore 126 is adapted to receive percutaneous visualization device 104. A hinge 122 pivotably interconnects first section 118 and second section 120. First section 118 and second section 120, however, can be pivotably or slidingly coupled to each other by any known or later developed means. In the depicted embodiment, hinge 122 is disposed at proximal end 116a of cannula 116. Nonetheless, the location of hinge 122 is not a vital feature of the cannula 116 inasmuch as first section 118 is pivotably secured to second section 120.

First section 118 and second section 120 of cannula 116 are pivotably movable between an open position (as shown in FIG. 2) and a closed position (as depicted in FIG. 3). For example, first and second sections 118, 120 can be closed by retracting cannula 116 relative to trocar 102 such that pivot 122 is within trocar 102. In addition, first and second sections 118, 120 may be spring-loaded in the open or closed positions or connected to a linkage to facilitate opening and closing of sections 118, 120. In use, a user should place cannula 116 in the open position before inserting percutaneous visualization device 104 therethrough. After placing visualization device 104 into cannula 116, first and second sections 118, 120 can be moved to the closed position to clean at least a portion of the percutaneous visualization device 104.

To accomplish its function, cleaning device 114 further includes a cleaning swab 124 positioned at the distal end 116b of cannula 116. Cleaning swab 124 can be specifically disposed in first section 118, second section 120, or both. Regardless of the specific location of cleaning swab 124, cleaning swab 124 is configured to pivot into a position to clean at least a portion of percutaneous visualization device 104. In one embodiment, cleaning swab 124 cleans distal end 104b of percutaneous visualization device 104 when first section 118 and second 120 pivot into the closed position towards the direction indicated by arrow "A", as illustrated in FIG. 3.

Since cleaning swab 124 is configured to clean device 100, it can be constructed of any material suitable for cleaning a surface. In one embodiment, for instance, cleaning swab 124 is composed of an elastomeric membrane. Another embodiment of the present disclosure includes cleaning swab 124 made of a fluid absorbable material. The cleaning swab 124 of this particular embodiment can be impregnated with a cleaning fluid to enhance its sanitizing capabilities. Moreover, the cleaning fluid can be adapted to clean and defog viewing lens 112 of percutaneous visualization device 104.

Referring to FIG. 4, cleaning swab 124 also incorporates a slit 130 extending at least along a length thereof. During use, slit 130 expands upon passage of percutaneous visualization device 104 therethrough, thereby allowing percutaneous visualization device 104 to reach its intended surgical site. As percutaneous visualization device 104 passes through slit 130, cleaning swab 124 cleans at least a portion of percutaneous visualization device 104. Slit 130, however, is not an essential characteristic of the present disclosure and can be replaced with any other structural feature that allows passage of percutaneous visualization device 104. In a similar vein, cleaning swab 124 may comprise a pad, sponge, a wiper, or any apparatus suitable for cleaning. Cleaning swab 124 may provide a surface which is self clearing of debris in order to allow repeated use of cleaning swab 124 during the course of an operation. For example, the surface of cleaning swab 124 may be porous or have multiple ridges to trap debris away from the wiping surface. Also, cleaning swab 124 may present multiple surfaces, such as laminated surfaces which may be pealed back to present fresh cleaning surfaces. In the case of laminated surfaces, the laminations may be retained on a portion of cleaning swab 124 to allow the used surfaces of swab 124 to be removed with the rest of trocar 102 rather than individually.

In operation, a user initially inserts a first percutaneous visualization device 104 through trocar 102 to ocularly inspect the internal structures and features of the human body while cannula 116. The user then retracts the first percutaneous visualization device 104. While retracting the first percutaneous visualization device 104, bodily fluids and debris may enter bore 126 of cannula 116. Before inserting a second percutaneous visualization device 104 through trocar 102, the user should place trocar 102 in its open position. Subsequently, the user introduces the second percutaneous visualization device 104 through trocar 102. During insertion, bodily fluids and debris deposited in trocar 102 may attach to the second percutaneous visualization device 104. To clean the second percutaneous visualization device 104, the operator moves cannula 116 into the closed position. Concomitantly, cleaning swab 124 pivots into a position suitable to clean at least a portion of the second percutaneous visualization device 104 upon insertion into cannula 116. The user may iterate this process to clean other visualization devices.

With reference to FIGS. 5-5B, the present disclosure contemplates another embodiment of a surgical instrument 200. Surgical instrument 200 includes percutaneous visualization device 204 adapted for visual inspection of a human body's internal features. In the depicted embodiment, percutaneous visualization device 204 is an endoscope, but any other instrument, such as a laparoscope, can be employed as long as they are configured for ocular inspection of the inner structures of a body. Percutaneous visualization device 204 includes a proximal end 204a and a distal end 204b. A handle 208 is disposed on proximal end 204a of percutaneous visualization device 204 while a viewing lens 212 is positioned on distal end 204b of percutaneous visualization device 204. A tubular member 210 interconnects handle 208 and viewing lens 212 and is configured to transmit light therethrough. Percutaneous visualization device 204 can further include a camera configured to transmit video signals to an external monitor. The present disclosure also envisions other kinds of visualization devices having other elements and features.

In addition to percutaneous visualization device 204, surgical instrument 100 includes a trocar 202. Trocar 202 has a proximal end 202a and a distal end 202b. It is envisioned that trocar 202 can be a sleeve, a sheath or any other apparatus capable of providing percutaneous access into a body. In particular, trocar 202 has an insufflation valve 206 or any other device designed for providing fluid access to trocar 202. Insufflation valve 206 is disposed at the proximal end 202a of trocar 202. Trocar 202 additionally includes a handle 228 disposed at the proximal end 202a of trocar 202.

In the embodiment illustrated in FIG. 5, trocar 202 includes a cannula 216 having a proximal end 216a and a distal end 216b. Cannula 216 has a seal 214 at least partially disposed therein and a bore 226 extending therethrough. Specifically, seal 214 is positioned on distal end 216b and is configured to clean at least a portion of percutaneous visualization device 204 upon insertion and retraction in cannula 216. In use, seal 214 minimizes contamination of cannula 216 during the insertion and extraction of percutaneous visualization device 204. In one embodiment, seal 216 is a watertight seal adapted to significantly reduce the amount of bodily fluids and debris that access bore 226 of cannula 216 during use. Seal 214 can be made of any material suitable for cleaning such as an elastomeric membrane. In an embodiment, seal 214 is composed of a fluid absorbable material. Seal 214 can be impregnated with a cleaning fluid to enhance its cleaning capabilities. A slit 230 of seal 214 allows translation of percutaneous visualization device 204 beyond the boundaries of cannula 216. In use, slit 230 expands upon passage of percutaneous visualization device 204 therethrough.

In an alternative embodiment, cannula 216 includes at least one cleaning surface 222 positioned at the distal end 216b in lieu of seal 214, as shown in FIG. 6-6B. Cleaning surface 222 is configured to clean at least a portion of percutaneous visualization device 204 upon insertion and retraction in cannula 216. In the depicted embodiment, cleaning surface 222 is composed of seal wipes. Despite the latter, one skilled in art will readily recognize that cleaning surface 222 can consist of any other suitable cleaning apparatus. Further, cleaning surface 222 can be made of any suitable material. For example, a fluid absorbable material may form cleaning surface 222. Moreover, cleaning surface 222 can be impregnated with a cleaning solution.

Returning to FIG. 5, cannula 216 further includes a cleaning surface 218 on at least a portion of an inner surface 220. Cleaning surface 218 is configured to clean at least a portion of percutaneous visualization device 204 upon insertion and retraction in cannula 216. Any material suitable for cleaning can be used to make cleaning surface 218. For instance, in one embodiment, cleaning surface 218 is composed of an elastomeric membrane. In another embodiment, cleaning surface 218 can be made of a fluid absorbable material. The fluid absorbable material may be impregnated with an appropriate cleaning fluid. Aside from the material mentioned above, those skilled in the art will understand that cleaning surface 218 can consist of any suitable material configured to clean a medical device.

During use, surgeons introduce a first percutaneous visualization device 204 through trocar 202 to visually inspect the internal features of a human body. Users then remove the first percutaneous visualization device 204 from trocar 202. While the first percutaneous visualization device 204 is extracted from trocar 202, cleaning surface 218 and cleaning seal 214 sanitize at least a portion of the first percutaneous visualization device 204. Additionally, slit 230 of cleaning seal 214 of cleaning seal 214 expands while the first percutaneous visualization device 204 is disposed therethrough. Once the first percutaneous visualization device 204 is removed from trocar 204, slit 230 contracts and minimizes contamination inside cannula 216, as shown in FIGS. 5A and 5B. Thereafter, surgeons insert a second percutaneous visualization device 204 through trocar 202. During insertion of the second percutaneous visualization device 204, cleaning surface 218 and cleaning seal 214 clean percutaneous visualization device 204. Slit 230 of cleaning seal 214 expands upon passage of the second percutaneous visualization device 204 therethrough while, at the same time, minimizing contamination of the cannula 216. The embodiment shown in FIGS. 6-6B operates substantially similar to the embodiment illustrated in FIGS. 5-5A. In the former embodiment, cleaning surface 222 deforms to allow passage of percutaneous visualization device 204 during operation, as seen in FIGS. 6A and 6B.

With reference of FIGS. 7 and 8, another embodiment of the presently disclosed surgical instrument is designated as reference numeral 300. Surgical instrument 300 includes a percutaneous visualization device 304. Although the drawings depict percutaneous visualization device 304 as an endoscope, it is envisioned that it can be a laparoscope or any other suitable instrument adapted for visual inspection of a body's internal features. In particular, percutaneous visualization device 304 includes a handle 308, a tubular member 310, and a viewing lens 312. Handle 308 is positioned at a proximal end 304a of percutaneous visualization device 304. Lens 312, on the other hand, is disposed on a distal end 304b of percutaneous visualization device 304. Tubular member 310 interconnects handle 308 and lens 312 and is adapted to transmit light therethrough. In one embodiment, percutaneous visualization device 304 has a camera configured to transmit video signals to an external monitor. Percutaneous visualization device 304, however, is not restricted to a particular structural configuration.

Surgical instrument 300 additionally includes a trocar 302 having a proximal end 302a and a distal end 302b. Trocar 302 includes an insufflation valve 306 or any other suitable apparatus designed to provide fluid access to trocar 302. Insufflation valve 306 is disposed on proximal end 302a. Moreover, trocar 302 includes a handle 328 disposed at the proximal end 302a. During use, a surgeon may grab handle 328 to control and guide trocar 302.

Aside from handle 328, trocar 302 has a cannula 316. Cannula 316 includes a proximal end 316a, a distal end 316b, and a bore 326 extending therethrough. Bore 326 is adapted and dimensioned to receive percutaneous visualization device 304 and a sleeve 330.

Sleeve 330 surrounds at least a portion of percutaneous visualization device 304, thereby preventing, or at least minimizing, contamination of percutaneous visualization device 304 during insertion and retraction in cannula 316. In use, sleeve 330 can be inserted and removed from cannula 316. Numerous materials can be used to form sleeve 330. For example, sleeve 330 can be constructed of an impermeable material, a fragile material, flexible material, or a combination thereof. There may be multiples sleeves 330 disposed in layers surrounding at least a portion of percutaneous visualization device 304. In an embodiment, sleeve 330 is made of a polymer. In any case, one skilled in the art will recognize that sleeve 330 can be made of any suitable material.

In operation, a user covers percutaneous visualization device 304 with sleeve 330. Then, the user introduces percutaneous visualization device 304 through trocar 302 until it reaches its intended destination. At this time, bore 326 of cannula 316 may contain bodily fluids and debris. Nevertheless, sleeve 330 covers percutaneous visualization device 304 during insertion into cannula 316 and protects it from contamination. Once visualization instrument reaches the desired location, the operator peels sleeve 330 back or perforates sleeve 330 by moving percutaneous visualization device 304 distally, as shown in FIG. 7. Thereafter, the surgeon can use percutaneous visualization device 304 to observe a patient's inner cavity. In the instance of multiple sleeves 330, the outermost intact sleeve may be peeled back to preventing, or at least minimize, ongoing contamination of percutaneous visualization device 304 during the operation.

It will be understood that various modifications can be made to the embodiments disclosed herein. Therefore, the above description should not be construed as limiting, but merely as exemplifications of embodiments. Those skilled in the art will envision other modifications within the scope and spirit of the claims appended hereto.

What it is claimed:

1. A cleaning device for use with a percutaneous visualization device, comprising:
   a cannula having a proximal end and a distal end, the cannula including a first section pivotably connected to a second section, and the cannula including a hinge interconnecting the first section and the second section, wherein the hinge is disposed adjacent a proximal portion of the first section and adjacent a proximal portion of the second section; and
   a cleaning swab positioned at the distal end of the cannula, the cleaning swab being configured to pivot into a position to clean at least a portion of a percutaneous visualization device upon insertion into the cannula.

2. The cleaning device of claim 1, wherein the hinge is disposed at the proximal end of the cannula.

3. The cleaning device of claim 1, wherein the cleaning swab is made of a fluid absorbable material.

4. The cleaning device of claim 1, wherein the cleaning swab is impregnated with a cleaning fluid.

5. The cleaning device of claim 1, wherein the cleaning swab is laminated.

6. The cleaning device of claim 1, wherein the cleaning swab is selectively pivotable by a user into a position to clean at least a portion of a percutaneous visualization device.

7. The cleaning device of claim 1, wherein the first section of the cannula is pivotably connected to the second section of the cannula about a single pivot location.

8. The cleaning device of claim 1, wherein a proximal end of the first section of the cannula is substantially longitudinally aligned with a proximal end of the second section of the cannula, and wherein a distal end of the first section of the cannula is substantially longitudinally aligned with a distal end of the second section of the cannula.

* * * * *